US006100089A

United States Patent [19]
Reddy et al.

[11] Patent Number: 6,100,089
[45] Date of Patent: *Aug. 8, 2000

[54] RAPID SCREENING MUTAGENESIS AND TERATOGENESIS ASSAY

[75] Inventors: Vermuri B. Reddy, Westboro; Cha-Mer Wei, Worcester, both of Mass.

[73] Assignee: Exemplar Corporation, Worcester, Mass.

[ * ] Notice: This patent is subject to a terminal disclaimer.

[21] Appl. No.: 08/049,834

[22] Filed: Apr. 19, 1993

Related U.S. Application Data

[63] Continuation of application No. 07/847,839, Mar. 9, 1992, abandoned, which is a continuation of application No. 07/435,085, Nov. 13, 1989, abandoned, which is a continuation-in-part of application No. 07/276,055, Nov. 25, 1988, abandoned.

[51] Int. Cl.⁷ .............................. C12N 5/10; C12N 15/01; C12N 15/85; C12Q 1/68
[52] U.S. Cl. .................................. 435/325; 435/4; 435/8; 435/29; 435/320.1; 435/455
[58] Field of Search ............................ 435/172.3, 240.2, 435/320.1, 317.1, 325, 455, 4, 8, 29; 935/13, 111

[56] References Cited

U.S. PATENT DOCUMENTS

| | | | |
|---|---|---|---|
| 4,569,916 | 2/1986 | Penman et al. | 436/64 |
| 4,792,520 | 12/1988 | Stambrook et al. | 435/6 |
| 4,870,009 | 9/1989 | Evans et al. | 435/69.4 |
| 4,873,191 | 10/1989 | Wagner et al. | 800/25 |
| 4,873,316 | 10/1989 | Meade et al. | 800/7 |
| 5,510,099 | 4/1996 | Short et al. | 424/9.2 |

FOREIGN PATENT DOCUMENTS

| | | |
|---|---|---|
| 87107238 | 2/1987 | European Pat. Off. . |
| 88302174 | 2/1988 | European Pat. Off. . |
| PCT/GA87/00458 | 1/1988 | United Kingdom . |
| 8905864 | 6/1989 | WIPO . |

OTHER PUBLICATIONS

MacGregor et al., Somat. Cell Mol. Gen. 13(3):253–265 (1987).
Wilmut et al., New Scientist, Jul. 7, 1988, pp. 56–59.
Van Brunt, BioTechnology 6(10):1149,1151,1152,1154 (1988).
Ebert, Karl, "vol. I, *Comprehensive Biotechnology First Supplement vol. I Animal Biotechnology*" Chapter 3 "Gene Transfer Through Embryo Microinjection" (Tufts Univ. Schools of Med. and Vet Med.) (Published with approval of Pergamon Press).
Rafferty, K.A., "Methods in Experimental Embryology of the Mouse" (The Johns Hopkins Press, Baltimore and London).
Oda, et al., *Mutation Research* 147, 219–229 (1985).
Quillardet, et al., *Proc. Natl. Acad. Sci. USA* 79, 5971–5975 (1982).
Flint, *Teratology of the Limbs*, pp. 325, Merker, et al. editor (Walter de Gruyter & Co. Berlin 1980).
Flint, et al., J. Cell Sci. 61, 247 (1983).
Flint et al. *Concepts in Toxicology* vol. 3, In vitro Embryotoxicity and Teratogenicity Tests, Homburger, et al. editor (Karger,Basel1985).
Toxic. Appl. Pharmac.76, 383 (1984).
Flint et al *J. Appl. Toxicol.* 4, 109 (1984).
Keller, *Molecular Toxicology* 1, 261–276 (1987).
Norton and Coffin, *Mol. Cell. Biol.* 5, 281–290 (1985).
deWet, et al., *Mol. Cell. Biol.* 7, 725–737 (1987).
Coulondre and Miller, *Mol. Biol.* 117, 577 (1977).
Miller, *Ann. Rev. Genet.* 17, 215 (1983).
Hu and Davidson, *Cell* 48, 555 (1987).
Brown, et al., *Cell* 49, 63 (1987).
Allen, et al., *Nature* 333, 852–855 (1988).
DuBridge, et al., *Mol. Cell. Biol.* 7, p. 379–387 (1987).
Figge, et al., *Cell*, vol. 52, p. 713–722 (1988).
Flint, et al., *Biol. and App. Pharma.*76, p. 383–395 (1984).
Fuerst, et al., *Proc. Natl. Acad. Sci. USA*, vol. 86, pp. 2549–2553 (1989).
Goring, et al., *Science*, vol. 235, pp. 456–458 (1987).
Lebkowski, et al., *Proc. Natl. Acad. Sci. USA*, vol. 82, pp. 8606–8610 (1985).
Lebkowski, et al., *Mol. and Cell. Biol.*, vol. 6, pp. 1838–1842 (1986).
Liu, et al., *Proc. Natl. Acad. Sci.USA*, vol. 86, pp. 9951–9955 (1989).

*Primary Examiner*—Scott D. Priebe
*Attorney, Agent, or Firm*—Arnall Golden & Gregory, LLP

[57] ABSTRACT

A rapid, sensitive, and quantitative method and assay system using transgenic animal cells and adult or embryonic transgenic animals to rapidly screen compounds for mutagenic or teratogenic activity. Each cell from a cell culture, a differentiated tissue from an animal or an animal embryo contains a target gene and a reporter gene, both including an animal promoter/enhancer, a coding sequence and a transcription termination signal, so that they are capable of expression in animal cells. The product of the target gene is capable of regulating expression of the reporter gene through interaction with a regulatory sequence in the reporter gene. In the preferred embodiment, the target gene lacI (lac repressor) is coupled to the reporter gene lacZ encoding beta-galactosidase, which is easily detectable by cytochemical or histochemical procedures. When the animal cell is exposed to a compound causing a mutation either altering expression of the target gene or altering the operator of the reporter gene, the reporter gene is expressed.

5 Claims, 7 Drawing Sheets

RAPID SCREENING MUTAGENESIS AND TERATOGENESIS ASSAY

"This is a continuation of application Ser. No. 07/847,839 filed Mar. 9, 1992 now abandoned, which is a continuation of application Ser. No. 07/435,085 filed on Nov. 13, 1989, now abandoned which is a continuation-in-part of U.S. Ser. No. 07/276,055 filed Nov. 25, 1988, now abandoned".

BACKGROUND OF THE INVENTION

This application generally relates to genetic engineering and specifically involves the use of engineered animal cells containing an expressible target gene coupled to an expressible reporter gene to assay for mutagens.

Toxicity testing is required for many new drugs and agents released into the environment or work place. Compounds must generally be screened for damage to the embryo (teratogenesis activity) and for damage to the differentiated animal (carcinogenesis or mutagenesis activity).

Classically, compounds have been assayed for mutagenic activity using short term tests employing bacterial cell systems (STT) or animal studies. Most animal studies are conducted using the protocol for rodents developed by the National Cancer Institute in the early 1970s, reported by Sontag, et al., in *U.S. Dep. Health Educ. Welfare Publ. (NIH) Carcinog. Tech. Rep. Serv.* 1,76 (1976). However, the correlation between the results obtained in the two systems is poor and hard to measure objectively. For example, as reported by Tennant, et al., in *Science* 236, 933–941 (1987), there is only approximately 60% concordance between four widely used STTs and rodent carcinogenicity results. The four tests that were compared were the Salmonella mutagenesis, SAL, (described in Haworth, et al., *Environ. Mutagen.* 5 suppl. 1)3 (1983) and Mortelmans, et al. *Toxicol. Appl. Pharmacol.* 75, 137 (1984), etc.; chromosome aberrations in Chinese hamster ovary cells, ABS; sister chromatid exchanges in Chinese hamster ovary cells, SCE, (both described in Galloway, et al. *Environ. Mutagen.* 7, 1 (1985), and Galloway, et al. *Environ. Mutagen* (1987); and mouse lymphoma cell, MOLY, (described in Myhr, et al., *Evaluation of Short-Term Tests for Carcinogens: Report of the International Programme on Chemical Safety's Collaborative Study on in vitro Assays*, vol. 5 of *Progress in Mutation Research Series*, pp. 55–568, J. Ashby, et al. Editors (Elsevier, Amsterdam, 1985)) assays.

A recent variation of the SAL, or Ames, in vitro assay was reported by Oda, et al., in *Mutation Research* 147, 219–229 (1985). Oda, et al., introduced a fused umuC'-'lacZ gene into *Salmonella typhimurium*. The umu operon in *Escherichia coli* is responsible for chemical and radiation mutagenesis and is inducible by DNA-damaging agents. Induction of umu by the compound being tested is determined by production of beta-galactosidase activity resulting from expression of lacZ. A similar modification to the SOS chromotest to detect DNA-damaging agents, described by Quillardet, et al., *Proc. Natl. Acad. Sci.* (USA) 79, 5971–5975 (1982), uses one of the SOS genes, sfiA, fused to lacZ on the chromosome of *E. coli*.

There are disadvantages associated with the rodent assays which are distinct from those identified with the in vitro assays. The most significant problem is the length of time required to demonstrate that a compound is carcinogenic, since the determination is made based on tumor growth following exposure to the compound being tested. In general, animal studies must extend over a period of at least 12 to 18 months before a compound can be determined not to be carcinogenic. Another problem is that it is impossible to distinguish between genotoxic compounds (those inducing mutations within the DNA which leads to tumor growth) and those which alter some other non-DNA factor which leads to tumor growth. Still another problem with the rodent assay is that it is qualitative, not quantitative, making it possible only to determine the minimum dosage which induces tumor growth in the species being tested under the assay conditions.

To date, very few in vitro assays screen compounds for non-genotoxic carcinogenic activity. One in vitro assay is described by Penman and Fey in U.S. Pat. No. 4,569,916. This method is based on induction of morphological changes in a cell line upon exposure to a compound to be tested.

Compounds have traditionally been screened for teratogenesis activity, or inhibition of cell differentiation, by exposing an embryo to the compound to be tested, then examining samples from different areas of development for aberrations or inhibition of growth. Detailed descriptions of systems in use are reported by Flint in *Teratology of the Limbs* edited by Merker, et al., p. 325 (Walter de Gruyter & Co., Berlin 1980) and Flint, et al., *J. Cell Sci.* 61, 247 (1983); *Concepts in Toxicology*, Vol. 3 *In Vitro Embryotoxicity and Teratogenicity Tests* edited by Homburger, et al., (Karger, Basel 1985); *Toxic. Appl. Pharmac.* 76, 383 and *J. Appl. Toxicol.* 4, 109 (1984). As reported, assays for cytotoxicity and for cell differentiation are made in vitro, with confirming studies in vivo. When in vitro studies are conducted, at a minimum, cells from the midbrain and forelimb areas must be exposed to the compound and examined for detrimental effects. Another in vitro teratogenicity assay is reported by Keller in *Molecular Toxicology* 1, 261–276 (1987) using vaccinia virus growth in primate cell cultures, stated to be equally predictive of human teratogenesis as the in vivo rodent assay.

None of the methods presently in use for screening for carcinogenesis or teratogenesis activity in vitro correlate very well with in vivo results, or, where results can be correlated, the tests are time consuming, cannot be quantitated easily and are limited in sensitivity.

It is therefore an object of the present invention to provide a simple, quantifiable, more sensitive assay for mutagens, carcinogens, and teratogens.

It is another object of the present invention to provide an accurate measure of mutagenesis or teratogenesis activity that can be accurately correlated with in vivo observations.

SUMMARY OF THE INVENTION

A method and assays using engineered animal cells, animal embryos or differentiated animals, carrying in each cell a target gene and a coupled reporter gene. Both the target gene and the reporter gene have been engineered by splicing to each coding sequence an animal promoter/enhancer and a transcription termination signal so that both genes can be expressed in animal cells. The target and reporter genes are introduced into a cultured animal cell or embryonic cell by DNA transfection or DNA microinjection, respectively. In the absence of mutation, the product of the target gene prevents expression of the reporter gene through interaction with a regulatory sequence in the reporter gene. When a mutation in the target gene occurs which results in production of inactive repressor or other regulatory proteins, the reporter gene is no longer repressed and the reporter protein is expressed.

The reporter genes encode biologically active proteins or antigens whose functions and presence can be easily monitored and quantitated using standard biochemical techniques. The target genes consist of those which encode regulatory proteins that can be linked to the control of reporter gene expression. These can be repressors or other regulatory molecules. The inactivation of a repressor gene by a mutagenic event causes the transcription and translation of a defective repressor protein that is unable to repress expression of the reporter gene. The same effect is produced by alteration of the operator region of the reporter gene in a manner that prevents binding of the repressor protein. Expression of the reporter gene can then be monitored by assaying for defined functions of the gene product.

The reporter gene preferred at this time is the operator-containing E. coli lacZ gene which encodes beta-galactosidase. The target gene is the E. coli lacI gene which encodes the lac repressor. In the assay, the engineered animal cells are exposed to the mutagen. Prior to mutagenesis, expression of the beta-galactosidase gene is repressed by binding of the lac repressor protein to the lac operator. When a mutation event alters either the lacd gene, such that a defective lac repressor is produced, or alters the lac operator, the repressor can no longer bind to the operator. The beta-galactosidase gene is then expressed. The cells positive for beta-galactosidase are stained blue following addition of the substrate for beta-galactosidase, 5-bromo-4-chloro-3-indolyl-beta-D-galactopyranoside, "X-gal".

Detection of expression of the reporter gene is sensitive and quantitative, providing enhanced resolution of the effects of the compound being tested. There are a number of embodiments of the assay system based on selection of the reporter genes, the target genes, the promoters/enhancers and operator sequences, and the assay conditions. Three examples are provided, a transgenic animal cell system for in vitro analysis of mutagens, a transgenic animal system for in vivo analysis of mutagens, and a transgenic animal embryo system for in vivo analysis of teratogens.

BRIEF DESCRIPTION OF THE DRAWINGS

FIG. 3(a) is a photograph of control cells that remained colorless with X-gal substrate in the absence of IPTG, demonstrating lacZ repression by lacI repressor; and FIG. 3(b) is a photograph of cells stained blue with X-gal substrate in the presence of 15 mM IPTG, demonstrating lacZ expression.

FIG. 4(a) is a photograph of control cells not exposed to NMU and FIG. 4(b) is a photograph of cells which have been exposed to 150 μg NMU/ml cells in culture.

DETAILED DESCRIPTION OF THE INVENTION

Figure 1:
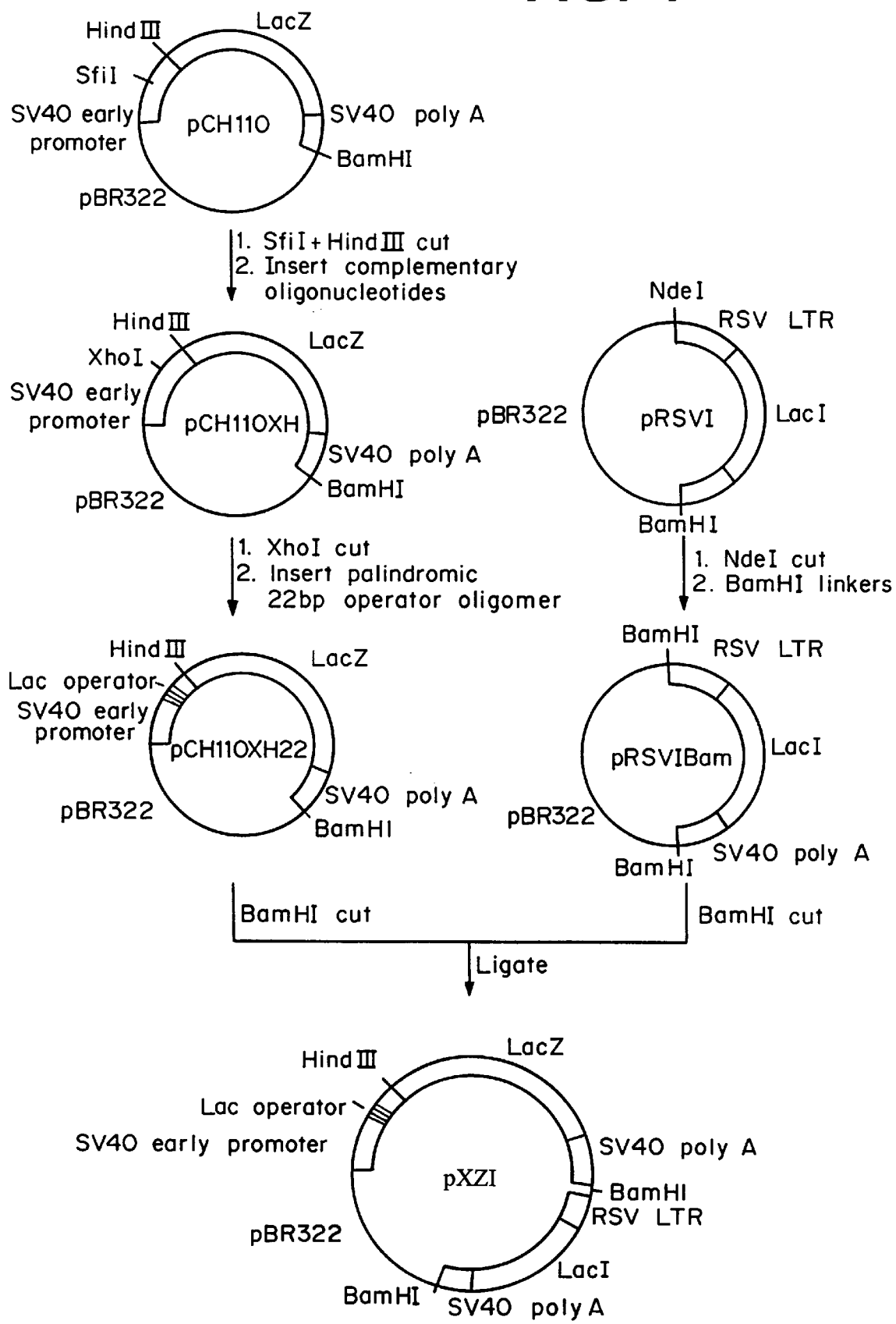
FIG. 1 is a schematic construction of an expression vector pXZI containing the complete coding sequence of the lac repressor flanked by the RSV-LTR promoter along with the SV40 polyadenylation site, which forms the functional transcription unit of the target gene, and the complete coding sequence of the beta-galactosidase enzyme flanked by the SV40 promoter along with the SV40 polyadenylation site which forms the functional transcription unit of the reporter gene.

As described below, a method has been developed which uses a set of two genes, a target gene and a reporter gene, incorporated into animals or animal cells to screen for compounds having mutagenic, carcinogenic or teratogenic activity. Exposure of the animals or animal cells to compounds having any of these activities causes mutations resulting in alterations in expression of the reporter gene. Both the target gene and the reporter gene constructs contain an animal promoter/enhancer, the protein coding sequence and the SV40 polyadenylation sequence.

This method has several advantages over the prior art methods of screening for compounds having mutagenic or teratogenic activity. The most significant advantage is the ease in detection and decrease in number of false positives. Although the mutation of genes encoding reporter proteins has previously been used to assay for mutagenic activity, the mutational event resulted in the protein not being expressed. Detecting a single cell, or even a few cells, not expressing a protein, while surrounded by cells which express the protein, is difficult, tedious, and subject to a high percentage of error. In contrast, in the present method, the mutational event ultimately results in the expression of a reporter molecule which would otherwise not be expressed, and which is readily detected.

As used herein, unless specifically stated otherwise, "animal cells" will be used to include cells in cell cultures, embryos, and differentiated animals. As also used herein, "mutagen" will be used to include toxins, carcinogens, teratogens, and other agents which alter DNA or RNA sequence or expression, unless stated otherwise.

The selection of reporter genes is based on the following criteria: (i) the reporter gene product cannot be detrimental or lethal to the transformed cells, (ii) the gene product should provide a simple and sensitive detection system for its quantitation, and (iii) non-transformed cells should have a low constitutive background of gene products or activities that will be assayed. Reporter genes which encode enzymes, antigens or other biologically active proteins which can be monitored easily by biochemical techniques are preferred. These include beta-galactosidase (Norton, P.A. and Coffin, J. M. *Mol. Cell. Biol.* 5, 281–290 (1985), peroxidase and luciferase (de Wet, J. R. et al. *Mol. Cell. Biol.* 7, 725–737 (1987). In the preferred embodiment, there is only one copy of the reporter gene in each animal cell. However, more than one copy may be utilized to increase the amount of reporter gene product. Although not usually required or desirable, it is also possible to include more than one type of reporter gene in the same animal cell.

The target gene is selected from the group of sequences which encode regulatory molecules that bind to a sequence controlling reporter gene expression. These can be repressors or other regulatory molecules, including anti-sense RNA. In the most preferred embodiment, the lacI repressor gene is used as a mutagenesis target. The inactivation of the repressor gene by a mutagenic event causes the transcription and translation of a defective repressor protein that is no longer able to repress expression of the reporter gene, the lacZ gene encoding beta-galactosidase. Alteration of the operator region for the reporter gene in a manner that prevents binding of the repressor protein produces the same effect. Derepression of the reporter gene can then be monitored by assaying for defined functions of the gene product.

The bacterial lac operator-repressor system is preferred because it is one of the most basic and thoroughly studied examples of a protein-nucleic acid interaction that regulates transcription of a gene, as described by Coulondre and Miller, *Mol. Biol.* 117, 577 (1977) and Miller, *Ann. Rev. Genet.* 17, 215 (1983). This bacterial regulatory system has been transfected into mammalian cells and expression detected by addition of an inducer, isopropyl beta-D-thiogalactoside (IPTG), as reported by Hu and Davidson, *Cell* 48, 555 (1987), and Brown, et al., *Cell* 49, 603 (1987). An important difference between previous uses of the lac operator-repressor system and the present method is that mutation rather than induction is used to derepress the reporter genes to express protein whose function is solely to serve as an indicator. Another difference is that, in the preferred embodiment, a single copy of functional target gene per cell is introduced into the genome.

For the repressor protein to control the expression of a reporter gene, the operator sequence has to be built into the reporter gene at the location between the transcription initiation site and the initiation codon ATG. Either an original lac operator sequence (5'-GGAATTGTGAGCGGATAACAATCC-3'), or a mutant lac operator, for example, a sequence which binds repressor eight times tighter (5'-ATTGTGAGCGCTCACAAT-3'), can be used in vector construction.

The lacI gene has a GTG initiation codon instead of ATG which is found in animal cells. The GTG codon can be converted to ATG by in vitro site specific mutagenesis, using the method of Hu and Davidson, *Cell* 48, 555 (1987). This modified lacI gene is then inserted into an appropriate expression vector which contains an eukaryotic promoter and the SV40 polyadenylation site.

Several promoters are good candidates for the construction of expression vectors. For the method of the present invention, two types of promoters are generally used. The first type consists of ubiquitous promoters such as the histone gene, ribosomal protein gene, and beta-actin gene. The second type consists of tissue specific promoters which include SV40 early promoter, Rous sarcoma virus (RSV) long terminal repeat (LTR) and cytomegalovirus (CMV) early gene promoter, etc. All of these promoters are known to drive gene expression in animal cells.

To construct cells for use as an in vitro mutagenesis model, strong viral promoters such as RSV-LTR are used to drive both the lacI and lacZ genes in animal cells. For an in vivo mutagenesis model to have broad application, most major organs of transgenic mice should express the mutagenesis target gene and reporter gene. Ubiquitous promoters and enhancers are preferred for use in construction of transgenic animal systems so that, irrespective of the peculiarities of the substances tested, the effect of the test compound on tissues of diverse organs and metabolic properties which contain the target gene can be detected. A preferred promoter for use as an ubiquitous promoter to drive the lacI gene is the histone 3.2 gene promoter. This is a transcriptionally very active, single copy gene in mice which is expressed at high levels and accounts for 30 to 40% of the histone H3 mRNAs isolated from a variety of mouse tissues.

In those mammalian cells and animal tissues where the histone 3.2 gene promoter does not result in optimum expression, other viral or cellular promoters can be selected to drive appropriate expression of the lacI gene. Examples of good candidates to be engineered into DNA constructs are the human ribosomal protein S14 gene, mouse ribosomal protein S16 gene, rat cytoplasmic beta-actin gene and human beta-actin gene. These genes have been cloned, their nucleotide sequences determined and they are available for use.

In the preferred embodiment, the reporter gene for use with the lacI regulatory gene is the gene encoding beta-galactosidase, derived from the bacterial lacZ gene. Expression of beta-galactosidase is readily detected using histochemical procedures. In another embodiment, the gene encoding SV40 large tumor (T) antigen is used as a reporter gene in place of the beta galactosidase gene, using an immunoperoxidase technique to detect the cells expressing the SV40 T antigen. A strategy similar to that employed for producing the lacZ reporter system is used to make the construct containing the complete sequence coding for SV40 T antigen for insertion into an appropriate expression vector. The complete transcription unit of SV40 T antigen is then physically linked to the functional transcription unit of lacI gene and transferred into appropriate cells to test for gene expression.

The theories and standard procedures for molecular cloning are described in *Molecular Cloninq*, edited by T. Maniatis, et al. Cold Spring Harbor, Laboratory, Cold Spring Harbor, N.Y.), *Lab Procedures in Molecular Biology*, edited by Ausubel, et al., (Greene Publishing Division of John Wiley, N.Y. 1987), and are generally known to those skilled in the art. Procedures include preparation of DNA and RNA, preparation of cloning vectors, ligation, transformation of competent cells, selection and screening by in situ filter hybridization, as described by David, et al., *Advanced Bacterial Genetics* (Cold Spring Harbor Laboratory, Cold Spring Harbor, N.Y.). In addition, techniques for separation of DNA by gel electrophoresis, mapping of restriction enzyme cleavage sites, and modification of DNA fragments by modifying enzymes are used. Most restriction enzymes, vectors, and reagents can be obtained from commercial companies. Common vectors and *E. coli* strains are used, for example, pBR322, pUC series, lambda-WES, M13mp, DH5, LE392, JM109 and HB101.

Chain termination methods are used for nucleotide sequence determination to confirm the DNA constructs at the splicing sites, as reported by Sanger, et al. *Proc. Natl. Acad. Sci. USA* 74, 5463 (1977). Many commercial suppliers provide both reagent kits and detailed protocols. Since most nucleotide sequences are known for the vectors, promoters and genes to be used, oligonucleotides of defined sequences are used as primers in sequencing experiments. These are typically 15 to 20 nucleotides long and very convenient for sequencing specific regions of interest, using the techniques of Messing, et al. *Nucleic Acids Res.* 9, 309 (1981). Either single-stranded or double-stranded DNA can be sequenced with this technique.

Oliogonucleotides to be used in DNA sequencing and as linkers are synthesized by an automated DNA synthesizer. This service can be obtained from commercial sources, such as Genetic Designs, Inc., Houston, Tex. The oligonucleotides greater than 30 nucleotides are then subjected to polyacrylamide gel electrophoresis to ensure purity.

DNAs are transfected into cells by one of several standard published procedures to form stable transformants, including, for example, calcium phosphate precipitation, DEAE-Dextran, electroporation, and protoplast fusion. These methods are described in detail as follows:

Calcium phosphate precipitation: DNAs are coprecipitated with calcium phosphate, according to the method of Graham and van der Eb in *Virology* 52, 456 (1973), before transfer into cells. 40–50 μg of DNA with salmon sperm or calf thymus DNA as a carrier is used for 0.5×10⁶ cells plated on a 100 mm dish. DNA is mixed with 0.5 ml of 2×Hepes solution (280 mM NaCl, 50 mM Hepes and 1.5 mM Na$_2$HPO$_4$, pH 7.0) to which an equal volume of 2×CaCl$_2$ (250 mM CaCl$_2$ and 10 mM Hepes, pH 7.0) is added. The solution with a white granular precipitate appearing after 30–40 minutes is distributed dropwise evenly on the cells and allowed to sit for 4–16 hours at 37° C. The medium is removed and the cells are shocked with 15% glycerol in PBS for 3 minutes. After removing the glycerol, the cells are fed with DMEM containing 10% fetal bovine serum and left in the incubator.

Protein samples are prepared for Western blot analysis by lysing cells and separating the proteins by SDS-PAGE. The proteins are transferred to nitrocellulose by electroblotting as described by Ausubel, et al., *Current Protocols in Molecular Biology* (John Wiley and Sons, 1987). After blocking the filter with instant nonfat dry milk (1 g in 100 ml PBS), primary antibody is added to the filter and incubated for 1 h at room temperature. The filter is washed thoroughly with phosphate buffered saline (PBS) and incubated with horseradish peroxidase—antibody conjugate for 1 h at room temperature. The filter is again washed thoroughly with PBS and the antigen bands are identified by adding diaminobenzidine.

Enzyme assays, protein purification, and other classical biochemical methods are employed. DNA and RNA are analyzed by Southern blotting and Northern blotting techniques. Typically, the samples to be analyzed are size fractionated by gel electrophoresis. The samples, DNA or RNA, in the gels are then transferred to nitrocellulose or nylon membranes by blotting techniques. The blots, which are replicas of sample patterns in the gels, are hybridized with probes in Southern and Northern analysis. Specific bands of interest can then be visualized by detection systems such as autoradiography.

DNA can also be transferred using the DEAE-Dextran method of Kimura, et al. *Virology* 49, 394 (1972) and Sompayrac, et al., *Proc. Natl. Acad. Sci. USA* 78, 7575 (1981); the electroporation method of Potter, *Proc. Natl. Acad. Sci. USA* 81, 7161 (1984), and the protoplast fusion method of Sandri-Goddin, et al. *Molec. Cell Biol.* 1, 743 (1981).

In the preferred embodiment of the assay, the engineered animal cells are exposed to the compound to be tested. Prior to mutagenesis, expression of the reporter gene is repressed by binding of the lac repressor to the operator of the reporter gene. When a mutation event alters the lacI gene such that a defective lac repressor is produced, or alters the operator, the repressor can no longer bind to the operator. The reporter gene is then turned on and directs the synthesis of the reporter protein.

The DNA constructs to be introduced into the genomes of animals are engineered using essentially the same methodology. These transgenic animals are used for in vivo mutagenesis tests. The preferred embodiment is a transgenic mouse or rat model that carries the lac repressor gene as the mutagenesis target coupled to an operator-containing reporter gene which can be turned on and expression of the reporter gene monitored, when the lac repressor gene is inactivated by mutagenesis. Both the target gene and reporter gene are of bacterial origin, but capable of being expressed in animal cells following insertion into animal gene expression vectors. This transgenic model allows simple and easy quantitation of mutagenesis events in vivo and therefore provides a more accurate risk assessment for toxic substances such as mutagens, carcinogens and teratogens than conventional rodent assays. The system is also more sensitive and rapid than standard rodent assays since mutations or alterations in the target gene can be detected at the DNA and cellular levels by histochemical techniques before tumor development.

The present invention is further described with respect to the following non-limiting examples.

EXAMPLE 1

In vitro Animal Cell Mutagenesis Assay.

(a) Construction of System.

Vector DNAs were generated based on plasmid components described in the literature or commercially available, as shown schematically in FIG. 1. PRSVI was obtained from Dr. Norman Davidson of California's Institute of Technology, Pasadena, Calif. This plasmid, as described by Hu, M. C., and Davidson, N., in *Cell*, 48,555 (1987), contains *E. coli* lacI repressor coding region linked to Rouse sarcoma virus (RSV) promoter and SV40 poly A. pCH110was described by Hall, C. V., et al., *J. Mol. Appl. Gen.*, 2,101 (1983), and provided by Dr. Frank Lee of DNAX, Palo Alto, Calif. The beta-galactosidase (lacZ) gene is fused to SV40 early promoter and SV40 polyadenylation site in this plasmid.

FIG. 1 outlines the insertion of an operator sequence and construction of a combination vector (pXZI). pCH110 was restricted with SfiI and HindIII and ligated to synthetic complementary oligomers:

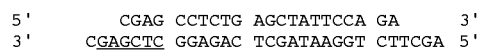

This procedure yielded plasmid derivative pCH110XH, having an XhoI site 18 nucleotides downstream from the TATTTA sequence in the SV40 early promoter, described by Reddy, V. B. et al., in *Science*, 200,494 (1978). lac operator DNAs can potentially be inserted at the XhoI, as well as the HindIII (42 nucleotides downstream of the TATTTA sequence), sites.

As a first step, PCH110XH was cut with XhoI and ligated to the oligomer shown below containing an eighteen nucleotide palindromic lac operator.

Figure 2:
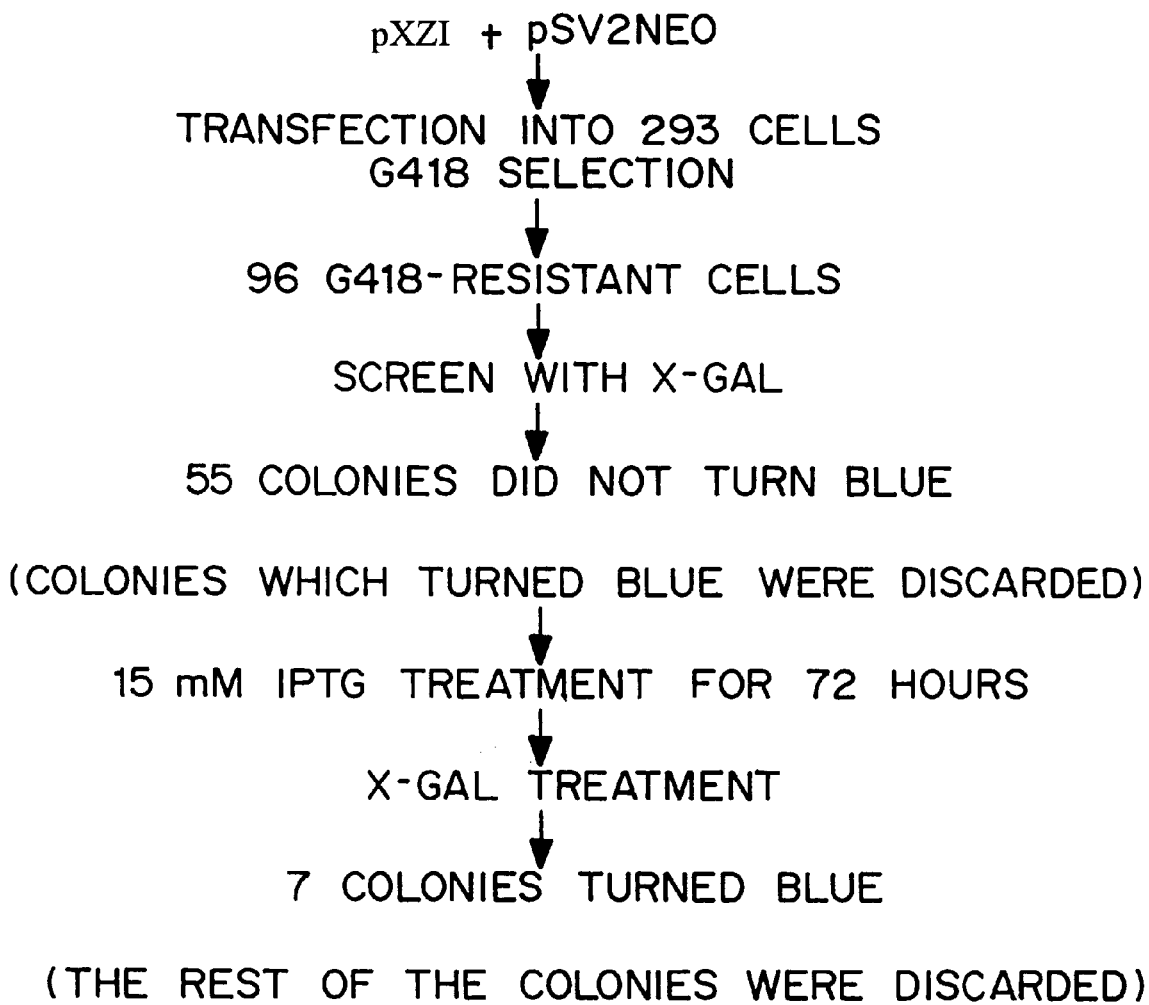
FIG. 2 is a schematic of the transfection of human embryonic kidney cells 293 with pXZI and pSV2NEO and isolation of cell lines positive for IPTG induction.

The resulting plasmid pCH110XH22 was cleaved with BamH1 and used to insert RSV lacI as a BamH1 fragment derived from pRSVI. The combination plasmid construct pXZI containing both the lacI and lacO-lacZ genes was used to transfect 293 cells, as diagrammed in FIG. 2. ATCC CRL-1573 (human embryonic kidney cells 293) are available from the American Type Culture Collection, Rockville, MD. Other cells such as ATCC CCL-T.1 (LLC-MK$_2$), that could be used, are also available from the ATCC.

The construct is co-transfected into the cells with a neo gene as the selection marker using known procedures, such as calcium phosphate precipitation method described above. The cell colonies resistant to the antibiotic G418 are detected by growth in the selection medium, cloned and analyzed for the presence of functional lac repressor and beta-galactosidase genes, as shown schematically in FIG. 2.

(b) Analysis and Characterization of System.

Transfected cells containing non-functional lac repressor gene and functional beta-galactosidase gene stain blue following addition of the substrate for beta-galactosidase, 5-bromo-4-chloro-3-indolyl-beta-D-galactopyranoside (X-gal), to cultures in the absence of inducer IPTG. The desired colonies, containing both functional lac repressor and beta-galactosidase genes, should stain blue following addition of IPTG and X-gal, remaining unstained if only X-gal is added. Successful expression of the lacI gene can also be demonstrated by Western blot analysis of lac repressor protein according to Sams, et al., *J. Biol. Chem.* 260, 1185 (1985) and by a filter-binding assay for repressor-operator DNA complexes according to Lin and Riggs, *J. Mol. biol.* 72, 671 (1972).

pXZI and pSV2neo DNAs were transfected into human embryonic kidney (293) cells using the calcium phosphate precipitation method. Following trypsinization 24 hours post transfection, the cells were plated at 1:10 dilution, and fed with medium containing G418 (350 µg/ml). 10 days later, 96 colonies were isolated with cloning rings and tested with X-gal for blue stain.

The 293 derived cells were rinsed with PBS (150 mM NaCl, 15 mM sodium phosphate, pH 7.3) and then fixed for 5 minutes at 4° C. in 2% formaldehyde and 0.2% glutaldehyde made with PBS. Following fixing and removal of fixing medium, the cells were washed with PBS and overlaid with a histochemical reaction mixture containing 1 mg X-gal/ml, 5 mM potassium ferricyanide, 5 mM potassium ferrocyanide, and 2 mM $MgCl_2$ in PBS. The X-gal was dissolved in dimethyl sulfoxide at 100 mg/ml concentration and diluted into the reaction mixture. The cells were incubated at 37° C. for 18–24 hours before they were examined for blue color.

55 colonies, which did not appear blue, were fed with medium containing 15 mm of IPTG (isopropyl beta-D-thiogalactoside). Seven colonies (designated XZI 1-7, XZI 1-12, XZI 1-13, XZI 2-9, XZI 2-13, XZI 3-4, and XZI 4-3) were selected which showed blue color in the presence of IPTG and remained colorless in the absence of IPTG.

Figure 3A:
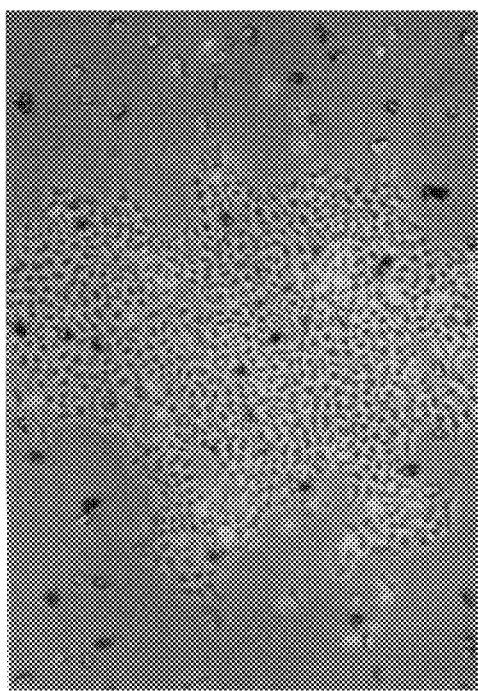
FIGS. 3(a) and 3(b) are photographs of XZI (293) cells carrying lacI and lacO-lacZ genes.
Figure 3B:
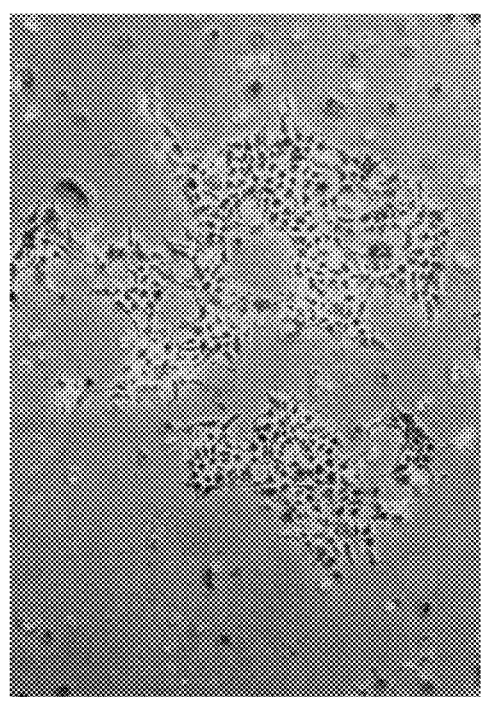

FIG. 3 demonstrates IPTG induction in one of the clones, showing that the lacI-lacO-lacZ system is functioning as expected and could be used for the in vitro mutagenesis assay. FIG. 3(*a*) is a photograph of the control cells, which remained colorless with X-gal substrate in the absence of the inducer IPTG. FIG. 3(*b*) is a photograph of the induced cells, stained blue with X-gal substrate in the presence of 15 mM IPTG, demonstrating lacZ expression.

Following successful expression of both lac repressor and beta-galactosidase genes in cultured cells, each of the colonies can be analyzed for the copy number of the introduced genes. Single copies of lacI gene per cell (diploid genome) are screened for by Southern blotting analysis of the genomic DNA. Cells with single copy are greatly preferred to cells containing more than one copy of functional lacI gene since these will require more than one mutational event to inactivate every copy of functional repressor gene and thereby to cause the depression of the reporter gene. Since the mutational event is detected by expression of the reporter gene, the number of copies of reporter gene is not as crucial, with more than one copy facilitating detection in some cases. The probability of obtaining single copy sequence is increased by using low concentrations of target DNA and sufficient carrier DNA to transfect recipient cells.

(c) Screening Compounds for Mutagenic Activity.

Nitrosomethylurea (NMU) can be employed as a model mutagen since it has been shown by Dubridge, et al., *Mol. Cell. Biol.* 7, 379 (1987) to readily induce mutations in the lacI gene in vitro. The cultured cells are treated with NMU for a specified period of time, and the cells screened for expression of the reporter gene. The frequency of mutations is quantified by scoring the number of beta-galactosidase positive cells among the total cells.

Similarly, the background frequency of mutations can be obtained by counting the number of beta-galactosidase positive cells present in cultures that are not exposed to the mutagen.

All seven cell lines were plated in duplicate at 30% confluence in 100 mm dishes. NMU was dissolved in PBS at 10 mg/ml concentrations and added directly to one of the two dishes of each cell line to a final concentration of 150 mg/ml. The dishes were left at 37° C. for 6 days while feeding with medium at three day intervals. If the cells became confluent they were subdivided to maintain semi-confluency and growth. X-gal histochemical reaction mixture was added after six days and the cells were visualized for blue colored-cells under a light microscope.

Figure 4A:
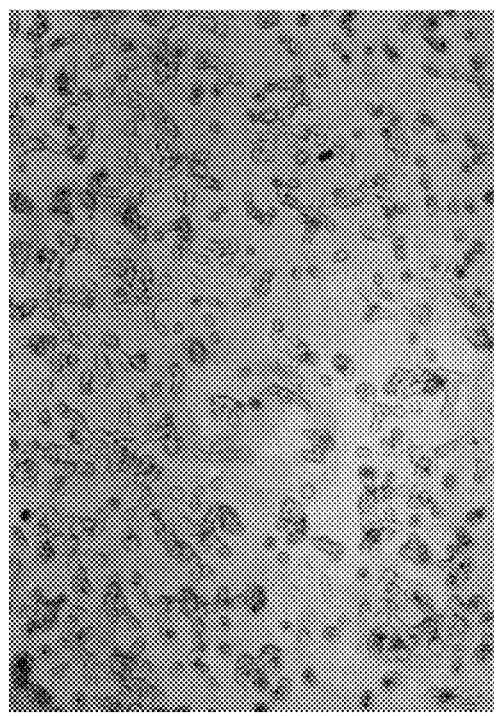
FIGS. 4(a) and 4(b) are photographs of XZI2-9 cells.
Figure 4B:
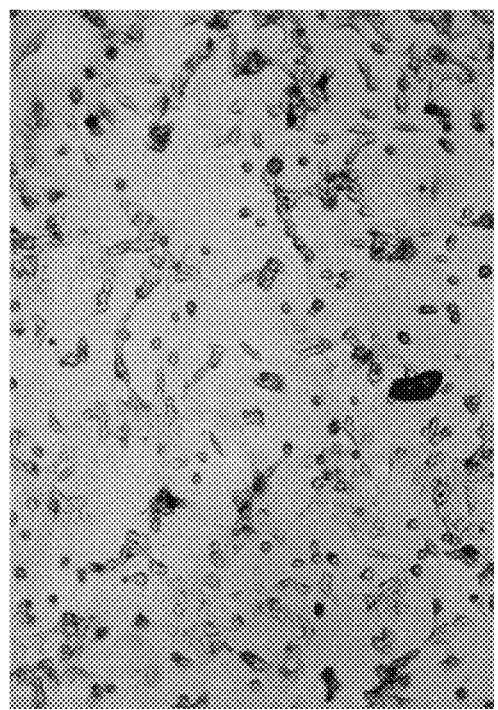

XZI 2–9 was found to yield 30 times more blue cells than the untreated control cells, as shown in FIG. 4, indicating the inactivation of lacI by NMU followed by derepression of lacZ. The other cells did not show an increase in blue cells over the untreated control cells, indicating that no mutation had occured that resulted in derepression of the beta-galactosidase gene.

Figure 5:
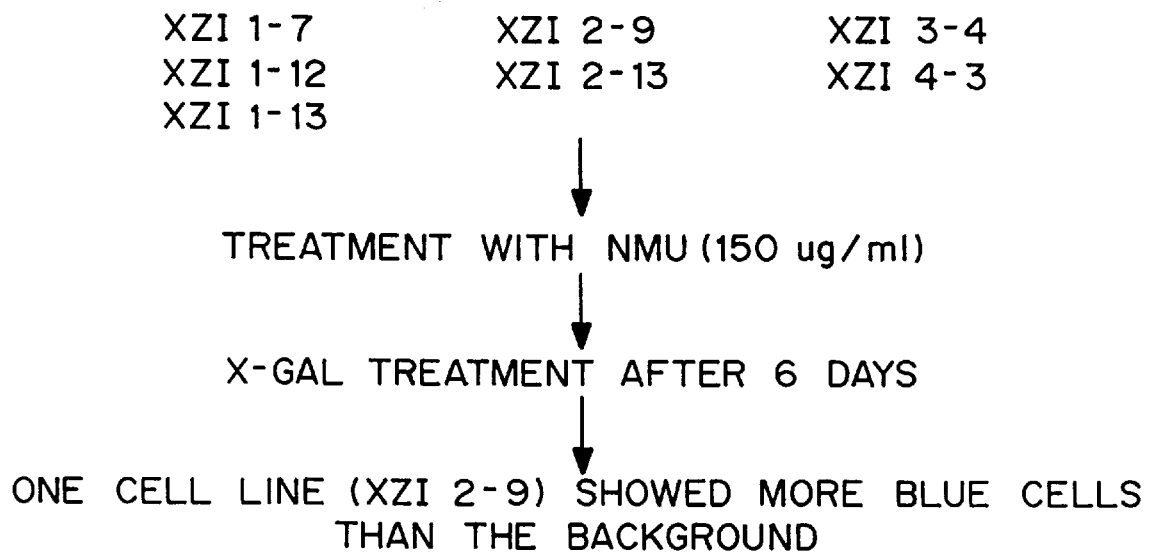
FIG. 5 is a schematic of a method for treating XZI cell lines with NMU and detecting more blue colored cells following X-gal supplementation than the control, indicating that those cells have undergone a mutagenic event.

FIG. 5 is a schematic of the process used to test compounds for mutagenesis. Cells which are capable of expressing beta-galactosidase in the presence of inducer are exposed to mutagen. After a period of days, cells are provided with X-gal substrate. The number of cells showing blue staining (corrected for background levels) is indicative of the mutagenic activity of the compound.

EXAMPLE 2

Transgenic Animal Mutagenesis Assay.

The first steps in producing transgenic animals for an in vivo assay are to prepare and detect activation of the beta-galactosidase reporter gene induced by mutation in lacI in mouse fibroblast cultures that have been successfully transfected with the coupled lacI-lacZ gene construct and subsequently exposed to a test mutagen, using the methodology described in Example 1. Controls consist of non-transfected cells and cells bearing the coupled genes that have not been exposed to the mutagen. The in vitro system is followed by the production of founder C57BL/6J transgenic mice bearing the coupled lacI-lacZ gene construct and, subsequently, production of transgenic offspring that contains the gene construct. Sexually mature, transgene-positive transgenic offspring serve as control and mutagenesis-test subjects.

(a) Preparation of DNA.

Figure 6:
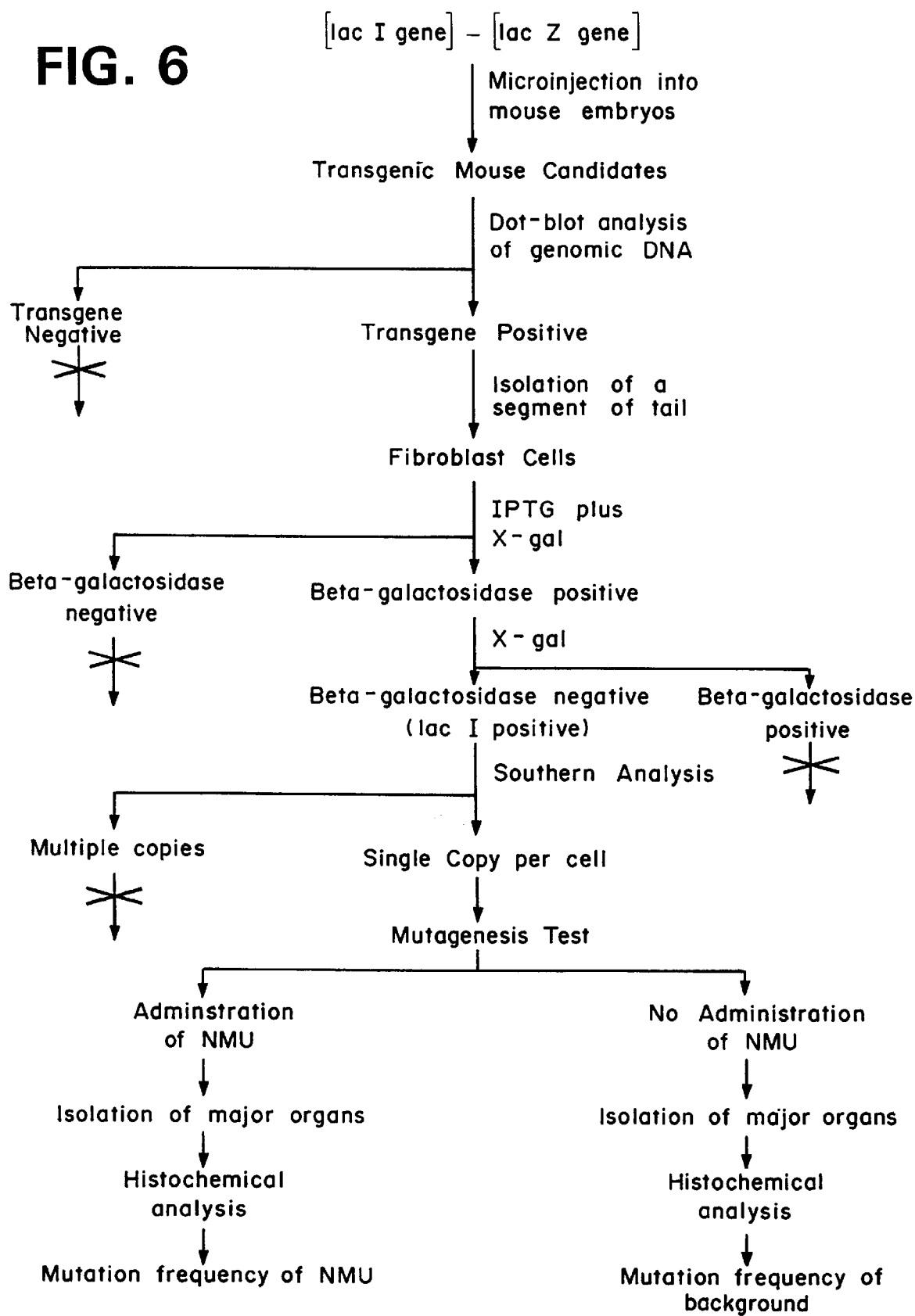
FIG. 6 is a schematic of a method for generating transgenic mice carrying the functional target gene and reporter gene and developing in vivo mutagenesis assays.

A DNA construct is prepared as described in Example 1 for use in making transgenic mice, as shown schematically in FIG. 6. The construct has two functional transcription units physically linked to each other, each containing a promoter/enhancer, a coding sequence and SV40 polyadenylation site. One is used to drive lac repressor gene expression; the other is used to drive the expression of the beta-galactosidase gene. The mouse histone-3.2 promoter can be used in the construct for ubiquitous expression of both lac repressor and beta-galactosidase genes.

The DNA fragment containing both the target gene, such as the lac repressor transcription unit, and the reporter gene, such as the beta-galactosidase transcription unit, or the SV40 T antigen unit, are excised from the vector by restriction enzyme digestion and isolated by gel electrophoresis and affinity column purification for microinjection, as follows. The fragments are separated on an agarose gel and the desired band recovered by electroelution. The DNA is extracted with phenol/chloroform, concentrated by ethanol precipitation, and further purified by binding and elution from Elutip-d columns. The DNA is then recovered by ethanol precipitation, dissolved in sterile 10 mM Tris pH 8, 1 mM EDTA and quantified by Hoechst dye fluorescence assay or spectrophotometry at 260 nm.

(b) Introduction of DNA into Embryos.

The theories and experimental procedures of transgenic mouse construction are described in "Manipulating the Mouse Embryo" by Brigid Hogan, Frank Costantini and Elizabeth Lacy (Cold spring Harbor Laboratory, Cold Spring Harbor, N.Y.) Mouse zygotes are collected from six week old C57B/6J females (Jackson Laboratory, Bar Harbor, Me.) that have been superovulated with 5 IU of Pregnant Mare's Serum Gonadotropin followed 48 h later by 51 U Human Chorionic Gonadotropin. Primed females are placed with C57BL/6J males and checked for vaginal plugs the following morning. Pseudopregnant females, used as recipients, are CD-1 females (Charles River Laboratories, Wilmington, Mass.) selected for estrus and placed with proven sterile vasectomized CD-1 males. Zygotes are collected in BMOC-2 medium modified to contain 5.1 g/l NaCl and 5 mg/ml bovine serum albumin. Cumulus cells are removed by treatment with hyaluronidase (Sigma Type IV, 300 IU/ml PBS with 1% PVP 40T, Sigma) diluted to 60 IU/ml in culture medium. Zygotes are washed twice in a 2 ml culture medium to remove debris. Approximately 2 pl of DNA solution is injected into the male pronucleus with approximately 50% surviving injection. Injected zygotes are incubated in 5% $CO_2$ in air at 37° C. until transferred to the oviduct of recipient females under tribromoethanol anaesthesia.

Integration of the gene construct can occur as a single copy or multiple copies that are generally in a head-to-tail tandem array, as reported by Palmiter, *Cell* 29, 701 (1982). Methodology for gene injection into the mouse embryo has been described by Brinster, et al., *Proc. Natl. Acad. Sci. USA* 82, 4438 (1985). Some of the more important factors for increasing the integration frequency are: the concentration of DNA injected may be a limiting factor in the efficiency of integration—a concentration of 1–2 ng/$\mu$l of DNA, or approximately 100–1,000 copies of the DNA fragment, appears to be optimum; a linear DNA molecule is more efficient if it is cut with endonucleases that result in non-blunt ends; and nuclear rather than cytoplasmic injection is required for high efficiency rates. Several other factors do not appear to effect the integration rate. Both female and male pronuclear injections can accommodate the injected DNA and result in comparable integration efficiencies. Pronuclear injections are not essential for integration to occur as injection of DNA into the nucleus of the two-cell embryo will also result in transgenic animals.

It has been suggested that the strain of mouse used could affect the efficiency of integration. For example, the C57 x SJL hybrid egg has been demonstrated to be more efficient than the inbred C57 strain. Comparable efficiencies have been achieved with inbred CD-1 mice (Charles River) as with the hybrids. Inbred C57BL/6J mice (Jackson Laboratories) can be used to eliminate segregation of potential background modifier genes. Inbred C57BL/6J black female mice are hormonally induced for superovulation by the administration of follicle stimulating hormone and luteinizing hormone. They are then mated with inbred male mice.

Fertilized one-cell embryos are flushed from the oviducts and treated with hyaluronidase to remove the cumulus oophorus cells from the embryos. The target DNA is then microinjected into the pronucleus of the one-cell embryo. About 100 copies of the lacI-lacZ DNA construct are injected into each embryo, which are then transferred to the oviducts of pseudopregnant foster mothers to complete the gestation period. The embryos are allowed to differentiate and develop into entire animals.

(c) Selection and analysis of transgenic mice for in vivo mutagenesis models:

Transgenic mice carrying single copies of coupled functional lacI-lacZ gene construct are screened and selected by the following procedures. A section of tail and/or one lobe of liver is used as a source for the isolation of genomic DNA. The copy numbers and structures of the transgenes are analyzed by Southern blotting with DNA from lac repressor or the reporter gene used as probes, as well as to ascertain whether any rearrangement or modification has occurred in the transgenes during the genesis of transgenic mice. Only the mice carrying single copies of the complete lacI-lacZ gene construct are subjected to further analysis.

Appropriate tissues are collected at autopsy from transgenic mice to assay for gene expression. RNA and protein are extracted from these tissues and used in Northern blot, Western blot and repressor function assays to detect expression of lac repressor gene in tissues of transgenic mice. Since the reporter gene should be repressed by the active lacI gene, expression of the reporter gene in tissues is not expected unless there is no functional lac repressor present or the inducer IPTG is added. Therefore, the use of the same promoter and enhancer in the construction of both the repressor and the reporter gene is an important strategy to avoid "uncoupling" of the two genes. The presence of functional lacI and lacZ genes in the tissues of transgenic mice can also be assayed with the procedures described in "Example 1, section (b)" using cells dissociated from tail tissues.

Figure 7:
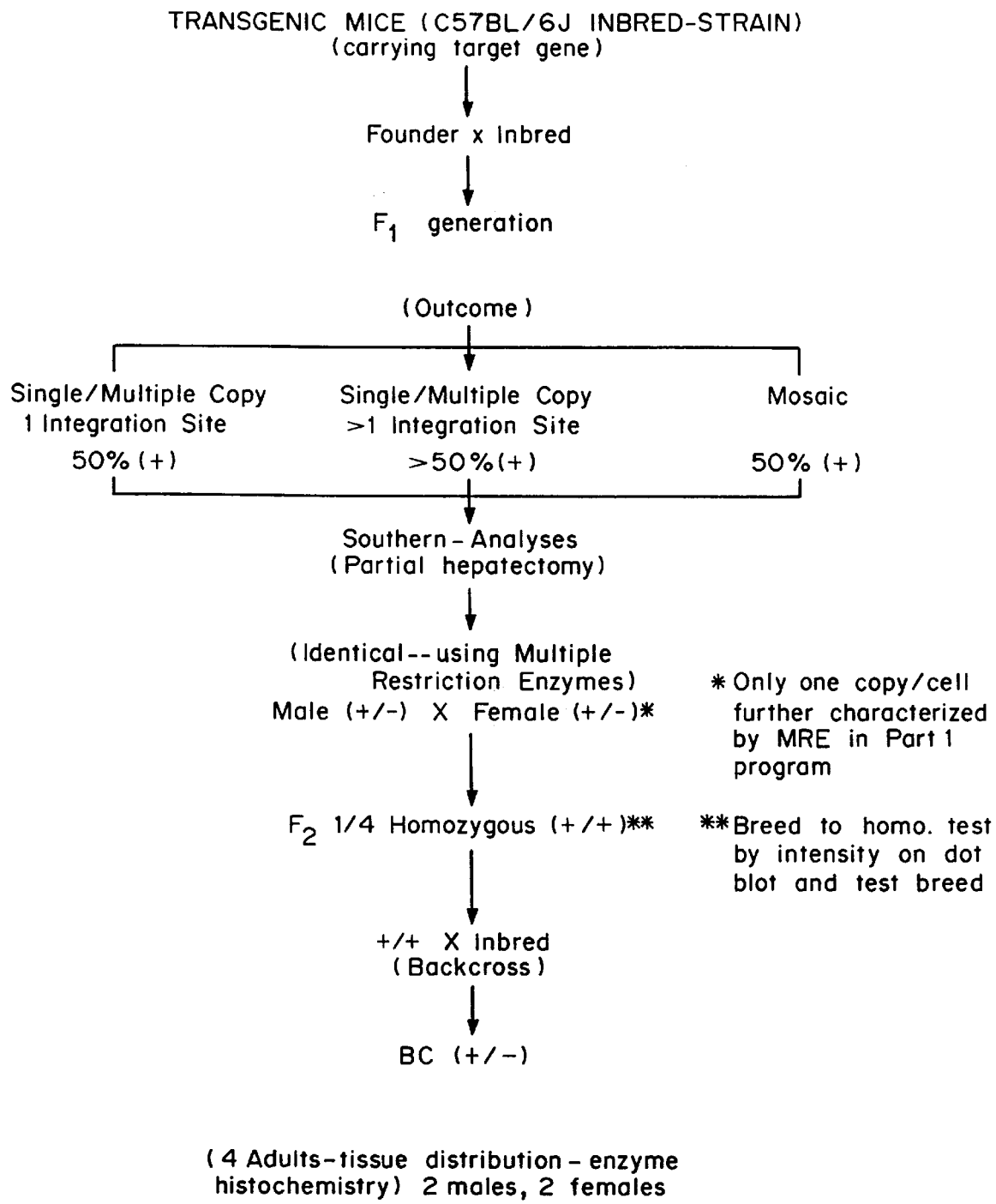
FIG. 7 is a schematic of a method for breeding and producing transgenic mice for use in in vivo assays.

Only the transgenic lines with one copy per cell of functional target gene are selected for further breeding to establish a homozygous transgenic line, as shown schematically in FIG. 7. The $F_1$ are bred with each other and the expected ¼ homozygous transgenic in the $F_2$ are identified by the intensity of the signal in Southern analysis. Homozygosity are confirmed by breeding tests and Southern analysis of the offspring. The homozygous offspring containing two copies of the transgene is bred to non-transgenic mates to produce heterozygous test animals for the mutagenesis assay.

(d) Analysis of transgenic animals exposed to compound to be tested.

Quantitative data can be obtained as to the localization and distribution of positive cells in the major organs of both control and mutagen-treated mice. Tissues from the following organs are selected for morphometric analysis. Brains, (tissues collected from the cerebellum, midbrain and forebrain), liver, spleen, kidney, left ventricle of the heart, lung, gonad, uterus, pancreas, fundus of the stomach, duodenum, ileum, colon and sternal bone marrow. Following fixation, tissue blocks are trimmed and the histochemical reaction for beta-galactosidase performed on 8 micron cryostat or 30 micron vibratome cuts to assure random sampling. Consecutive sections separated by 40 micron intervals are collected from each block. Positive cells are enumerated by digitizing morphometry using a biological image analyzer system and the Bio-quant II computer program (R&M Biometrics of Nashville, Tenn.). The hardware for this system consists of an image projecting camera mounted on a standard Zeiss binocular microscope, an Apple II microcomputer and a digitizing tablet. Using this system, the specimen is projected onto the computer screen and the operator selects and outlines the area that will be analyzed. Blood vessels and empty spaces, present as lumens of hollow organs, are outlined on the screen and the system is then instructed to subtract these areas from those that will be analyzed. Intense blue-stained cells are counted by using the digitizer and the numbers of positive cells per unit area of the tissue specimen under study is automatically computed. In this manner, the number of positive cells per unit area of a particular organ from an untreated or treated animal can be enumerated and resulting data statistically compared. A major added benefit of this system is that specific cell types that may be particularly susceptible to a given mutagen can be identified and quantified.

Histochemical analysis is performed on tissues from treated and untreated male and female transgenic mice with the same pedigree. Morphometric techniques can be used to produce quantitative data concerning the number of beta-galactosidase positive cells per organ and per animal sampled to provide information on the compound being tested, as well as the efficacy of the test procedure and the frequency of spontaneous background mutation in the transgenic animals. The expression of lacZ gene in cells is assayed by beta-galactosidase staining as follows:

Tissues are immersed in cold 4% paraformaldehyde to which 50 mM of $Na_3PO_4$ is added. This mixture is adjusted to pH 7.4. The immersed tissue is then fixed overnight in this mixture at 4° C. The activity of the enzyme is not impaired by this fixation. The tissues are subsequently rinsed in phosphate buffered saline (PBS) and 30 μm sections are cut on a vibratome or 8 μm sections are cut on a cryostat. The resultant sections are then incubated at 37° C., 5% $CO_2$ in 1 mg/ml X-gal, 5 mM K+ferricyanide, 5 mM K+ferrocyanide, 2 mM Mg $Cl_2$, 0.02% NP-40, 0.01% cholate in PBS at pH 7.3. The alkaline pH of this solution and the addition of $M_g^{++}$ is critical to avoid background staining of native galactosidase activity in lysosomes. The cells in a test tissue positive for beta-galactosidase will stain blue. The blue is visible within one hour and increases in intensity over the next 12 hours. This phenomenon can be visualized in either the free-floating vibratome sections or cryostat sections affixed to gelatin-coated glass slides. When the desired color intensity is achieved, vibratome sections are mounted onto slides in 0.1% $KCrSO_4$ and 1% gelatin and dried on a slide warmed at 37° C. for ½ hour. Sections are subsequently dehydrated and cleared in xylene for 2–3 minutes. Counter staining is performed using methyl green after which coverslips are placed over the sections. Paraffin sections of tissue whole-mounts can also be done since post-embedding in this material does not result in the loss of the blue positive staining. Paraffin embedded sections can therefore be stored and kept indefinitely as a permanent record for each test procedure.

If the SV40 large T antigen, or other antigen, is used as the reporter gene, a cytochemical-immunoperoxidase method, such as that described by Hanahan, Nature 315, 115 (1985), Ornitz, et al., Science 238,188 (1987); or Behringer, Proc. Natl. Acad. Sci. USA 85, 2648 (1988), is used to detect expression of reporter proteins.

EXAMPLE 3
Transgenic Animal Embryos to Assay for Teratogens.

Embryos of the transgenic animals carrying a target gene and a coupled reporter gene are used to screen for teratogens. This transgenic embryo model allows simple and rapid quantitation of mutagenesis events in a system which is similar to the living human embryo and should provide a more accurate assessment of the risk of a compound being teratogenic than currently used methods.

Transgenic animals, such as mice and pigs carrying the lacI gene coupled to the lacZ gene, generated by the procedures described in detail in Examples 1 and 2, are used to generate transgenic offspring as test animals. Embryos isolated at different stages from pregnant female transgenic animals with successful gene expression are exposed to the agent to be tested, and analyzed for expression of the reporter gene.

For example, a 10-mm transgenic pig embryo which has been developing for a gestation period of 20–21 days and contains the rudiments of almost all adult structures is exposed to a potential teratogen. The mutation events caused by teratogenic substances will inactivate the target gene and turn on the reporter gene in certain cells/tissues of the embryo. These cells/tissues can be detected using histochemical analysis as described above or by Allen, N. D., et al., in "Transgenes as probes for active chromosomal domains in mouse development", Nature 333, 852–855 (1988) when the reporter protein is beta galactosidase, or as otherwise appropriate for the reporter protein.

Modifications and variations of the methods and assay systems, transgenic animals and animal cells carrying target genes coupled to reporter genes for testing for mutagens and teratogens, will be apparent to those skilled in the art from the foregoing detailed description of the invention. Such variations and modifications are intended to come within the scope of the appended claims.

We claim:
1. A system for rapid screening for compounds which cause a mutation or alteration in expression of a nucleic acid sequence in an animal cell comprising:

an animal cell in culture containing a stably integrated lacI gene, a stably integrated lac operator sequence and a stably integrated reporter gene of a different origin than the animal cell, wherein the lacI gene is present in the chromosome as a single copy and the lac operator sequence is operably linked to and regulates expression of the reporter gene when lacO is bound by the inhibitory molecule expressed from the lacI gene and wherein mutation of the lacI gene results in detectable expression of the reporter gene in the animal cell.

2. The system of claim 1 wherein the reporter gene is operably linked to an eukaryotic promoter and a transcription termination signal.

3. The system of claim 2 wherein the reporter gene product is selected from the group consisting of proteins and nucleic acid sequences complementary to reporter gene sequence, wherein the proteins are selected from the group consisting of enzymes and antigen.

4. The system of claim 3 wherein the reporter gene product is selected from the group consisting of beta-galactosidase, luciferase, peroxidase and immunochemically detectable antigens.

5. The system of claim 1 further comprising at least one promoter driving expression of the reporter gene selected from the group consisting of the histone 3.2 gene, human ribosomal protein S14 gene, mouse ribosomal protein S16 gene, beta-actin gene, cytomegalovirus early gene promoter, SV40 early promoter, Rous sarcoma virus long terminal repeat and Moloney leukemia virus long terminal repeat.

* * * * *